(12) United States Patent
Yuan et al.

(10) Patent No.: US 8,404,863 B2
(45) Date of Patent: Mar. 26, 2013

(54) TETRAHYDROINDOLES HAVING SPHINGOSINE-1-PHOSPHATE RECEPTOR ACTIVITY

(75) Inventors: Haiqing Yuan, Irvine, CA (US); Richard L. Beard, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 168 days.

(21) Appl. No.: 12/810,099

(22) PCT Filed: Dec. 17, 2008

(86) PCT No.: PCT/US2008/087205
§ 371 (c)(1),
(2), (4) Date: Sep. 22, 2010

(87) PCT Pub. No.: WO2009/085847
PCT Pub. Date: Jul. 9, 2009

(65) Prior Publication Data
US 2011/0003876 A1    Jan. 6, 2011

Related U.S. Application Data

(60) Provisional application No. 61/018,860, filed on Jan. 3, 2008.

(51) Int. Cl.
*C07D 209/04* (2006.01)
*C07D 209/10* (2006.01)

(52) U.S. Cl. ...................................... 548/452
(58) Field of Classification Search .................... 548/452
See application file for complete search history.

(56) References Cited

FOREIGN PATENT DOCUMENTS

| WO | WO0198301 | 12/2001 |
|---|---|---|
| WO | WO02064616 | 8/2002 |
| WO | WO03062252 | 7/2003 |
| WO | WO03062392 | 7/2003 |
| WO | WO03074008 | 9/2003 |
| WO | WO2004071442 | 8/2004 |
| WO | WO2005014572 | 2/2005 |
| WO | WO2005040169 | 5/2005 |
| WO | WO2005058848 | 6/2005 |
| WO | WO2007095561 | 8/2007 |
| WO | WO2007112322 | 10/2007 |

OTHER PUBLICATIONS

Jean D'Angelo, β-Keto -δ-Valerolactone : Synthesis aJ)d Use as Methylvinylketone Anion "Equivalent in Michael Additions", Tetrahedron Letters, Vol.32, No. 26, pp. 3063-3066, 1991.
Sarah Spiegel "Sphingosine 1-Phosphate, a Key Cell Signaling Molecule", The Journal of Biological Chemistry, vol. 277, No. 29, Issue of Jul. 19, 2002; pp. 25851-25854, 2002.
"Prodrugs and Drug Delivery Systems," which is a chapter in Richard B. Silverman, Organic Chemistry of Drug Design Drug Action, 2d Ed., Elsevier Academic Press: Amsterdam, 2004, pp. 496-557.
L. Leyssens, M. Van B0ven; "Biotransformation of Hexapropymate in Man" Laboratory of Toxicology of the Catholic University of Louvain, Pharmazie 38 (1983),Belgium.
William A. Carroll; "Synthesis and Structure-Activity Relationships of a Novel Series of Tricyclic Dihydropyridine-Based KATP Openers That Potently Inhibit Bladder Contractions in Vitro", J. Med. Chem. 2004, 47, 3180-3192, Jul. 24, 2003.
Michael D. Davis; "Sphingosine 1-Phosphate Analogs as Receptor Antagonists"; The Journal of Biological Chemistry, vol. 280, No. 11, Issue of Mar. 18, pp. 9833-9841, 2005.
Albert Padwa; "Novel Rhodium(I1)-Catalyzed Cycloaddition Reaction of &-Diazo Keto Amides", J. Am. Chem. Soc. 1990, 112, 2037-2038.
Hugh Rosen, "Chemical Approaches to the Lysophospholipid Receptors"; Prostaglandins & other Lipid Mediators 77 (2005) 179-184.
Claus Herdeis; Eine dreistufige Synthese der 6-Aminolaevulinsaure[1]) (A Three-Step Synthesis of 8-Aminolnevulinic Acid); Institut fur Pharmazie und Lebensmittelchemie der Universitat Munchen, Sophienstraae 10, 8OOO Munchen 2, Eingegangen am Jan. 28, 1983.

*Primary Examiner* — Shawquia Young
(74) *Attorney, Agent, or Firm* — John E. Wurst; Doina G. Ene; Allergan, Inc.

(57) ABSTRACT

Compounds are disclosed herein having the formula (I). Therapeutic methods, compositions, and medicaments related thereto are also disclosed.

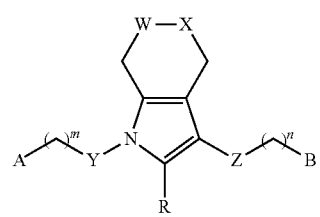

(I)

10 Claims, No Drawings

TETRAHYDROINDOLES HAVING SPHINGOSINE-1-PHOSPHATE RECEPTOR ACTIVITY

CROSS REFERENCE TO RELATED APPLICATIONS

This is a national stage application under 35 U.S.C. §371 of PCT patent application PCT/US2008/087205, filed on Dec. 17, 2008, which claims the benefit of U.S. Provisional Patent Application 61/018,860, filed Jan. 3, 2008, each of which is hereby incorporated by reference in its entirety.

BACKGROUND

Sphingosine is a compound having the chemical structure shown in the general formula described below, in which $Y^1$ is hydrogen. It is known that various sphingolipids, having sphingosine as a constituent, are widely distributed in the living body including on the surface of cell membranes of cells in the nervous system.

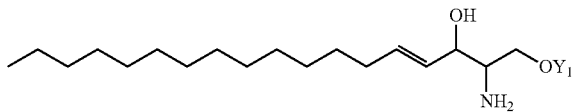

A sphingolipid is one of the lipids having important roles in the living body. A disease called lipidosis is caused by accumulation of a specified sphingolipid in the body. Sphingolipids present on cell membranes function to regulate cell growth; participate in the development and differentiation of cells; function in nerves; are involved in the infection and malignancy of cells; etc. Many of the physiological roles of sphingolipids remain to be solved. Recently the possibility that ceramide, a derivative of sphingosine, has an important role in the mechanism of cell signal transduction has been indicated, and studies about its effect on apoptosis and cell cycle have been reported.

Sphingosine-1-phosphate is an important cellular metabolite, derived from ceramide that is synthesized de novo or as part of the sphingomeyeline cycle (in animals cells). It has also been found in insects, yeasts and plants.

The enzyme, ceramidase, acts upon ceramides to release sphingosine, which is phosphorylated by sphingosine kinase, a ubiquitous enzyme in the cytosol and endoplasmic reticulum, to form sphingosine-1-phosphate. The reverse reaction can occur also by the action of sphingosine phosphatases, and the enzymes act in concert to control the cellular concentrations of the metabolite, which concentrations are always low. In plasma, such concentration can reach 0.2 to 0.9 μM, and the metabolite is found in association with the lipoproteins, especially the HDL. It should also be noted that sphingosine-1-phosphate formation is an essential step in the catabolism of sphingoid bases.

Like its precursors, sphingosine-1-phosphate is a potent messenger molecule that perhaps uniquely operates both intra- and inter-cellularly, but with very different functions from ceramides and sphingosine. The balance between these various sphingolipid metabolites may be important for health. For example, within the cell, sphingosine-1-phosphate promotes cellular division (mitosis) as opposed to cell death (apoptosis), which it inhibits. Intracellularly, it also functions to regulate calcium mobilization and cell growth in response to a variety of extracellular stimuli. Current opinion appears to suggest that the balance between sphingosine-1-phosphate and ceramide and/or sphingosine levels in cells is critical for their viability. In common with the lysophospholipids, especially lysophosphatidic acid, with which it has some structural similarities, sphingosine-1-phosphate exerts many of its extra-cellular effects through interaction with five specific G protein-coupled receptors on cell surfaces. These are important for the growth of new blood vessels, vascular maturation, cardiac development and immunity, and for directed cell movement.

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular disease. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

Fungi and plants have sphingolipids and the major sphingosine contained in these organisms has the formula described below. It is known that these lipids have important roles in the cell growth of fungi and plants, but details of the roles remain to be solved.

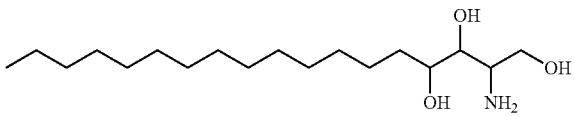 [SMILES: CCCCCCCCCCCCCCC(O)C(O)C(N)CO]

Recently it has been known that derivatives of sphingolipids and their related compounds exhibit a variety of biological activities through inhibition or stimulation of the metabolism pathways. These compounds include inhibitors of protein kinase C, inducers of apoptosis, immuno-suppressive compounds, antifungal compounds, and the like. Substances having these biological activities are expected to be useful compounds for various diseases.

DESCRIPTION OF THE INVENTION

Compounds are disclosed herein having the formula:

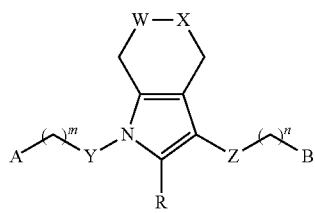

wherein m and n are independently 0, 1, or 2;
W and X are independently O, C=O, C($R^2$)$_2$, S, S(O), SO$_2$, N—$R^2$, or C=N$R^2$, wherein $R^2$ is independently H, OH, $C_{1-6}$ alkyl, —O—($C_{1-6}$ alkyl), or —NH—($C_{1-6}$ alkyl);

Y is $CH_2$, $C=O$, $-NHC(O)-$, or heteroaryl having a formula $C_{1-6}H_{0-11}N_{0-3}O_{0-2}S_{0-2}F_{0-1}Cl_{0-1}Br_{0-1}$;

Z is $CH_2$, CHOH, $C=O$, $-C(O)NH-$, $-NHC(O)-$, or heteroaryl having a formula $C_{1-6}H_{0-11}N_{0-3}O_{0-2}S_{0-2}F_{0-1}Cl_{0-1}Br_{0-1}$;

A and B are independently aryl or heteroaryl having a formula $C_{1-12}H_{0-29}N_{0-4}O_{0-6}S_{0-4}F_{0-6}Cl_{0-4}Br_{0-4}I_{0-4}$; and R is $C_{1-6}$ hydrocarbyl.

These compounds are useful for the treatment of diseases or conditions such as glaucoma, dry eye, angiogenesis, cardiovascular conditions and diseases, wounds, and pain. The compound is incorporated into a dosage form or a medicament and administered to the mammal, such as a person, in need thereof. Different types of suitable dosage forms and medicaments are well known in the art, and can be readily adapted for delivery of the compounds disclosed herein.

Thus, one embodiment is a method of treating a disease or condition comprising administering a compound disclosed herein to a mammal in need thereof, said disease or condition being selected from: glaucoma, dry eye, angiogenesis, cardiovascular conditions and diseases, wounds, and pain.

Another embodiment is use of a compound disclosed herein in the manufacture of a medicament for the treatment of a disease or condition in a mammal, said disease or condition being selected from: glaucoma, dry eye, angiogenesis, cardiovascular conditions and diseases, wounds, and pain.

For the purposes of this disclosure, "treat," "treating," or "treatment" refer to the use of a compound, composition, therapeutically active agent, or drug in the diagnosis, cure, mitigation, treatment, or prevention of disease or other undesirable condition.

Stable means that a compound is sufficiently stable to be stored in a bottle at room temperature under a normal atmosphere for at least 12 hours, or stable enough to be useful for any purpose disclosed herein.

Unless otherwise indicated, reference to a compound should be construed broadly to include pharmaceutically acceptable salts, prodrugs, tautomers, alternate solid forms, non-covalent complexes, and combinations thereof, of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion.

Unless stereochemistry is explicitly depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Hydrocarbyl is a moiety consisting of carbon and hydrogen, including, but not limited to:
  a. alkyl, which is hydrocarbyl that contains no double or triple bonds, such as:
    linear alkyl, e.g. methyl, ethyl, n-propyl, n-butyl, n-pentyl, n-hexyl, etc.,
    branched alkyl, e.g. iso-propyl, t-butyl and other branched butyl isomers, branched pentyl isomers, etc.,
    cycloalkyl, e.g. cyclopropyl, cyclobutyl, cyclopentyl, cyclohexyl, etc.,
    combinations of linear, branched, and/or cycloalkyl;
  b. alkenyl, which is hydrocarbyl having 1 or more double bonds, including linear, branched, or cycloalkenyl
  c. alkynyl, which is hydrocarbyl having 1 or more triple bonds, including linear, branched, or cycloalkynyl;
  d. combinations of alkyl, alkenyl, and/or akynyl $C_{1-6}$ hydrocarbyl is hydrocarbyl having 1, 2, 3, 4, 5, or 6 carbon atoms.

$C_{1-6}$ alkyl is alkyl having 1, 2, 3, 4, 5, or 6, carbon atoms such as methyl, ethyl, propyl isomers, butyl isomers, pentyl isomer, and hexyl isomers, etc.

Aryl is an aromatic ring or ring system such as phenyl, naphthyl, biphenyl, and the like. Heteroaryl is an aromatic ring or ring system containing one or more O, N, or S heteroatoms. Both aryl and heteroaryl may be substituted or unsubstituted, and unless otherwise indicated, "aryl" and "heteroaryl" should be taken to mean "substituted or unsubstituted aryl" and "substituted or unsubstituted heteroaryl." Similarly, unless otherwise indicated, any specific aryl or heteroaryl ring such as "phenyl," "pyridinyl," "thienyl," "furyl," etc., should be taken to mean "substituted or unsubstituted phenyl," "substituted or unsubstituted pyridinyl," "substituted or unsubstituted thienyl," "substituted or unsubstituted furyl," etc.

Examples of substituents may include the following, subject to the constraints defined herein for that particular moiety or substituent:
  A. Hydrocarbyl, including, but not limited to:
    a. alkyl, such as:
      linear alkyl, e.g. methyl, ethyl, n-propyl, n-butyl, n-pentyl, n-hexyl, etc.,
      branched alkyl, e.g. iso-propyl, t-butyl and other branched butyl isomers, branched pentyl isomers, etc.,
      cycloalkyl, e.g. cyclopropyl, cyclobutyl, cyclopentyl, cyclohexyl, etc.,
      combinations of linear, branched, and/or cycloalkyl;
    b. alkenyl, which is hydrocarbyl having 1 or more double bonds, including linear, branched, or cycloalkenyl
    c. alkynyl, which is hydrocarbyl having 1 or more triple bonds, including linear, branched, or cycloalkynyl;
    d. combinations of alkyl, alkenyl, and/or akynyl B. alkyl-CN, such as —CH$_2$—CN, —(CH$_2$)$_2$—CN; —(CH$_2$)$_3$—CN, and the like;

C. Hydroxy, —OH

D. hydroxyalkyl, i.e. alkyl-OH, such as hydroxymethyl, hydroxyethyl, and the like;

E. ether substituents, including —O-alkyl, alkyl-O-alkyl, and the like;

F. thioether substituents, including —S-alkyl, alkyl-S-alkyl, and the like;

G. amine substituents, including —NH$_2$, —NH-alkyl, —N-alkyl$^1$alkyl$^2$ (i.e., alkyl$^1$ and alkyl$^2$ are the same or different, and both are attached to N), alkyl-NH$_2$, alkyl-NH-alkyl, alkyl-N-alkyl$^1$alkyl$^2$, and the like;

H. aminoalkyl, meaning alkyl-amine, such as aminomethyl (—CH$_2$-amine), aminoethyl, and the like;

I. ester substituents, including —CO$_2$-alkyl, —CO$_2$-phenyl, etc.;

J. other carbonyl substituents, including aldehydes; ketones, such as acyl, including, acetyl, propionyl, and benzoyl substituents are contemplated;

K. fluorocarbons or hydrofluorocarbons such as —CF$_3$, CH$_2$CF$_3$, etc.; and

L. other nitrogen containing substituents such as —CN and —NO$_2$,

M. other sulfur containing substitutents such as sulfide, sulfonyl or sulfoxide;

N. aryl;

O. combinations of the above are also possible, subject to the constraints defined;

P. Alternatively, a substituent may be —F, —Cl, —Br, or —I.

In one embodiment, substituents can be any of —CF$_3$, —F, —Cl, —Br, and —I, or a substituent consisting of carbon, hydrogen, oxygen, nitrogen and sulfur.

In another embodiment, each substituent consists of a combination of the following moieties: hydrocarbyl; —O—, —S—, —SH, —OH, —NH$_2$, —NH—,

and —CN, which attaches only to carbon; and

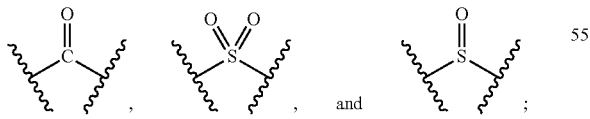

or the substituent is —CF$_3$, —F, —Cl, —Br, or —I.

In another embodiment, the substituents are selected from —CF$_3$, —F, —Cl, —Br, —I, C$_{1-3}$ alkyl, —OH, —SH, NH$_2$, —O—C$_{1-3}$ alkyl (i.e. —O-alkyl, where alkyl has 1-3 carbon atoms), —S—C$_{1-3}$ alkyl (i.e. —S-alkyl, where alkyl has 1-3 carbon atoms), —NO$_2$, —CN, and —CH.

Since m is 0, 1, or 2, the structures below are contemplated.

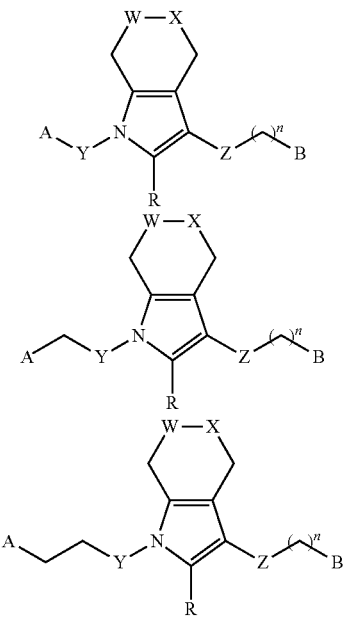

Since n is 0, 1, or 2, the structures below are contemplated.

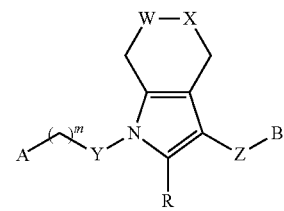

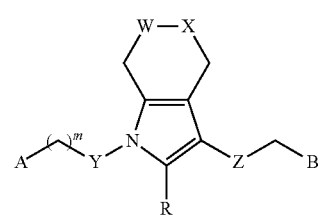

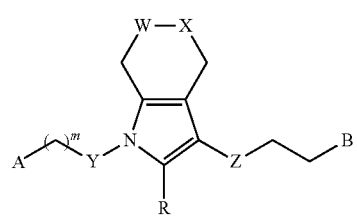

The fact that m and n are independently 0, 1, or 2 means that m and n may be the same or different. In other words, n may be 0, and m may be 0, 1, or 2; n may be 1, and m may be 0, 1, or 2; or n may be 2, and m may be 0, 1, or 2.

Similarly, W and X, A and B, and the two R$^2$ moieties of C(R$^2$)$_2$ may be the same or different with respect to one another.

W is O, C=O, C(R²)₂, S, S(O), N—R² or C=R². Thus, the structures below are contemplated.
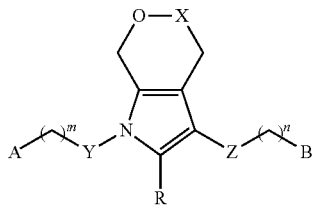
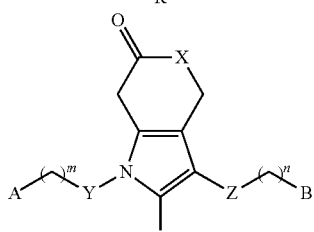
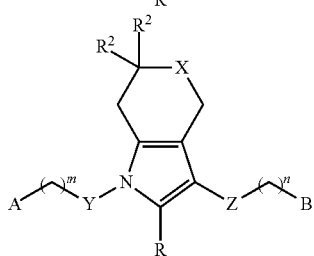
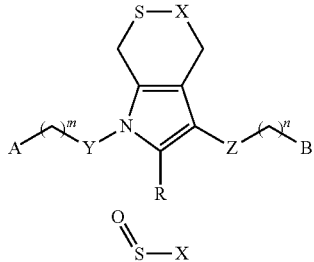
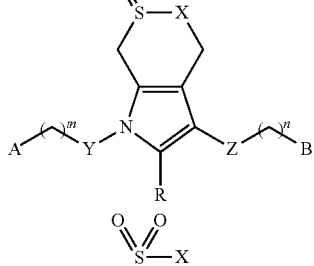
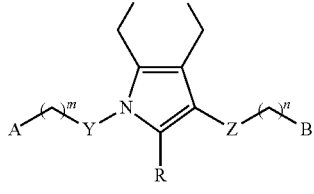
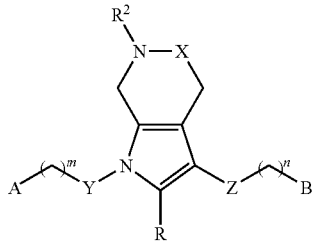
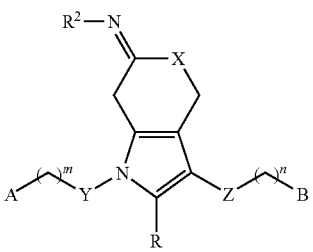
X is O, C=O, C(R²)₂, S, S(O), N—R² or C=R². Thus, the structures below are contemplated.
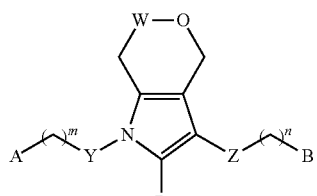
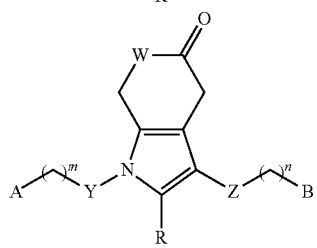
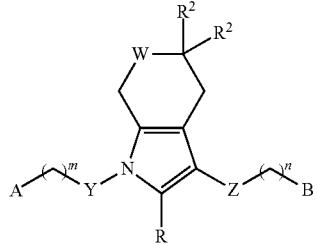
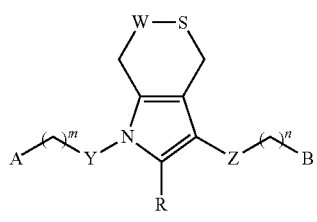
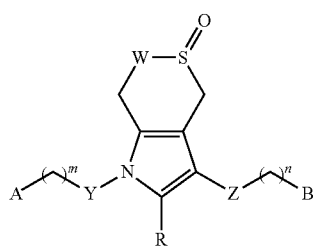

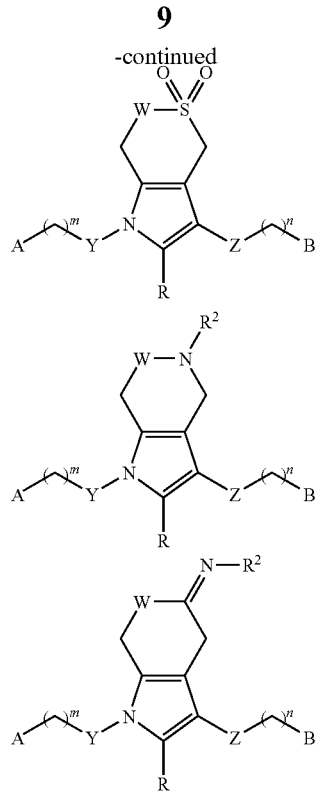

Y is CH$_2$, C=O, —NHC(O)—, or heteroaryl having a formula C$_{1-6}$H$_{0-11}$N$_{0-3}$O$_{0-2}$SO$_{0-2}$F$_{0-1}$Cl$_{0-1}$Br$_{0-1}$.

In one embodiment Y is CH$_2$.

In another embodiment Y is C=O.

In another embodiment Y is —NHC(O)—. "—NHC(O)—" means that the carbon atom attaches directly to the nitrogen of the ring, such that structures of the formula below are obtained.

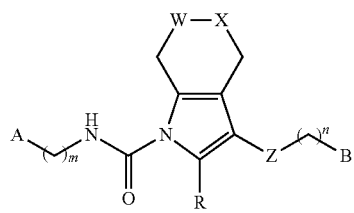

If Y is heteroaryl, the formula of Y, including both the ring and any substituents, is C$_{1-6}$H$_{0-11}$N$_{0-3}$O$_{0-2}$S$_{0-2}$F$_{0-1}$Cl$_{0-1}$Br$_{0-1}$. Thus, if Y is heteroaryl, it consists of from 1 to 6 carbon atoms, from 0 to 11 hydrogen atoms, from 0 to 3 nitrogen atoms, from 0 to 2 oxygen atoms, from 0 to 2 sulfur atoms, from 0 to 1 fluorine atoms, from 0 to 1 chlorine atoms, and from 0 to 1 bromine atoms.

The structures below are examples of useful heteroaryl moieties for Y.

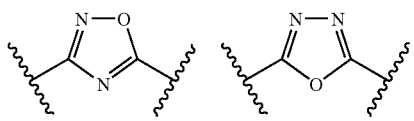

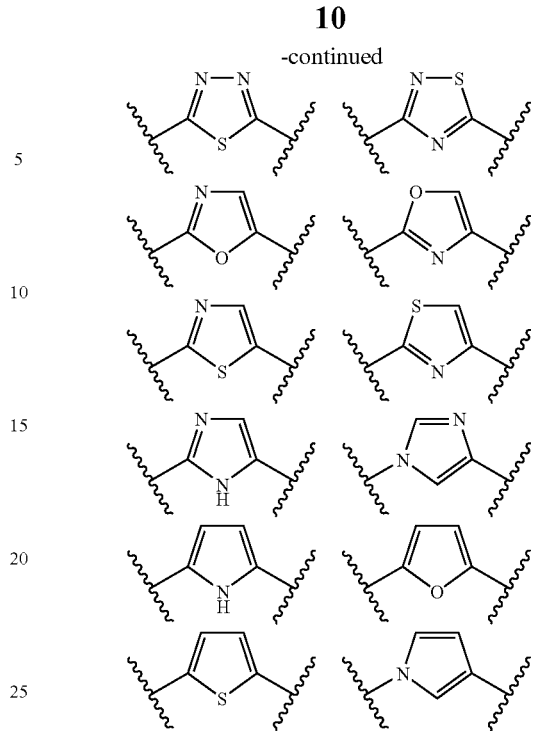

Z is CH$_2$, CHOH, C=O, —C(O)NH—, —NHC(O)—, or heteroaryl having a formula C$_{1-6}$H$_{0-11}$N$_{0-3}$O$_{0-2}$S$_{0-2}$F$_{0-1}$Cl$_{0-1}$Br$_{0-1}$.

In one embodiment, Z is CH$_2$.

In another embodiment, Z is CHOH.

In another embodiment, Z is —C(O)NH—. In other words, the structure below is contemplated.

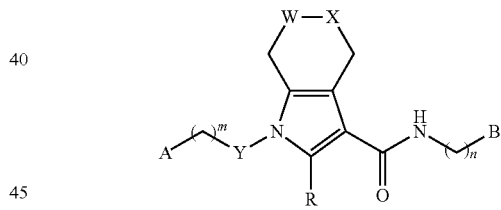

In another embodiment, Z is —NHC(O)—. In other words, the structure below is contemplated.

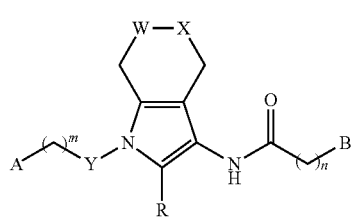

If Z is heteroaryl, the formula of Z, including both the ring and any substituents, is C$_{1-6}$H$_{0-11}$N$_{0-3}$O$_{0-2}$S$_{0-2}$F$_{0-1}$Cl$_{0-1}$Br$_{0-1}$. Thus, if Z is heteroaryl, it consists of from 1 to 6 carbon atoms, from 0 to 11 hydrogen atoms, from 0 to 3 nitrogen atoms, from 0 to 2 oxygen atoms, from 0 to 2 sulfur atoms, from 0 to 1 fluorine atoms, from 0 to 1 chlorine atoms, and from 0 to 1 bromine atoms.

The structures below are examples of useful heteroaryl moieties for Z.

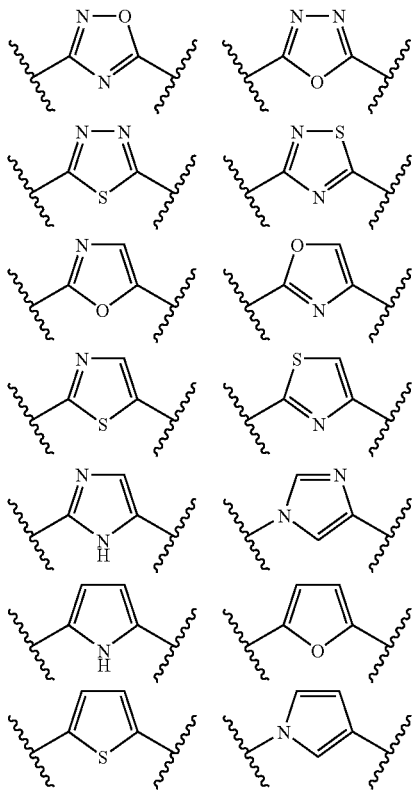

A is aryl or heteroaryl having a formula $C_{1-12}H_{0-29}N_{0-4}O_{0-6}S_{0-4}F_{0-6}Cl_{0-4}Br_{0-4}I_{0-4}$. Thus, A, including both the ring and any substituents has from 1 to 12 carbon atoms, from 0 to 29 hydrogen atoms, from 0 to 4 nitrogen atoms, from 0 to 6 oxygen atoms, from 0 to 4 sulfur atoms, from 0 to 6 fluorine atoms, from 0 to 4 chlorine atoms, from 0 to 4 bromine atoms, and from 0 to 4 iodine atoms. In one embodiment, A is phenyl, pyridinyl, thienyl, or furyl.

In one embodiment, A is phenyl.

In another embodiment, A is thienyl.

B is aryl or heteroaryl having a formula $C_{1-12}H_{0-29}N_{0-4}O_{0-6}S_{0-4}F_{0-6}Cl_{0-4}Br_{0-4}I_{0-4}$. Thus, B, including both the ring and any substituents has from 1 to 12 carbon atoms, from 0 to 29 hydrogen atoms, from 0 to 4 nitrogen atoms, from 0 to 6 oxygen atoms, from 0 to 4 sulfur atoms, from 0 to 6 fluorine atoms, from 0 to 4 chlorine atoms, from 0 to 4 bromine atoms, and from 0 to 4 iodine atoms. In one embodiment, B is phenyl, pyridinyl, thienyl, or furyl.

In one embodiment, B is phenyl.

In another embodiment, B is thienyl.

R is $C_{1-6}$ hydrocarbyl. In one embodiment, R is methyl, ethyl, a propyl isomer, a butyl isomer, a pentyl isomer, a hexyl isomer, or unsubstituted phenyl.

In one embodiment W is $CH_2$.

In another embodiment, X is $CH_2OH$, $C=O$, or $C=NHOH$.

In another embodiment, A is phenyl, thienyl, or pyridinyl.

In another embodiment, B is phenyl or pyridinyl.

In another embodiment, R is methyl, ethyl, n-propyl, or isopropyl.

Another embodiment is a compound having a formula:

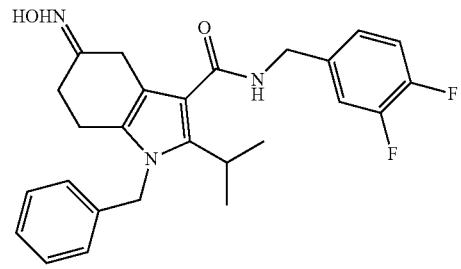

Other hypothetical examples of useful compounds are shown below.

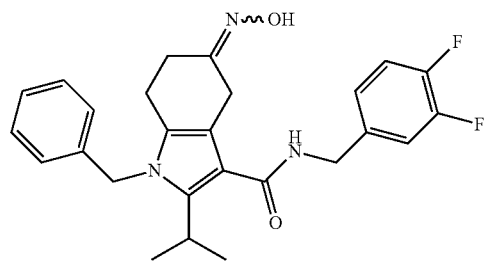

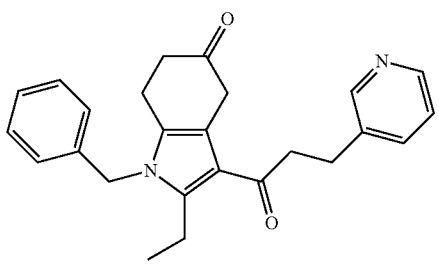

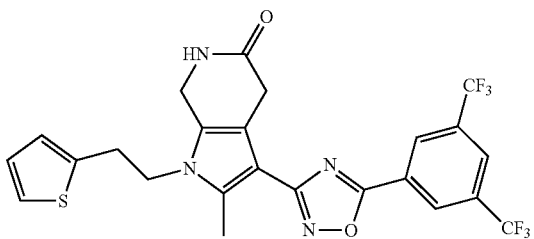

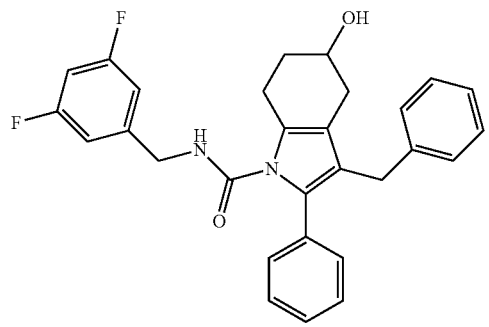

-continued

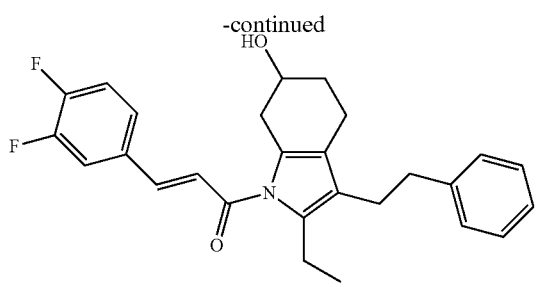

Synthetic Methods methods, where X' and W' are either X and W, protected forms of X and W, or moieties that are convertible to X and W using conventional methods. Examples of preparation of compounds such as A are described in *Pharmazie* (1983), 38(12), 851-4; *Journal of the American Chemical Society* (1990), 112(5), 2037-8; *Archiv der Pharmazie* (Weinheim, Germany), 317(4), 304-6; 1984; *Tetrahedron Letters*, 32(26), 3063-6; 1991; PCT Int. Appl., 2005014572, 17 Feb. 2005; and *Journal of Medicinal Chemistry*, 47(12), 3180-3192; 2004. R is incorporated via the protected amino aldehyde B that is condensed with A to form the core structure C. Different compounds for B may be obtained by reducing and protecting a readily available amino acid, or by base catalyzed

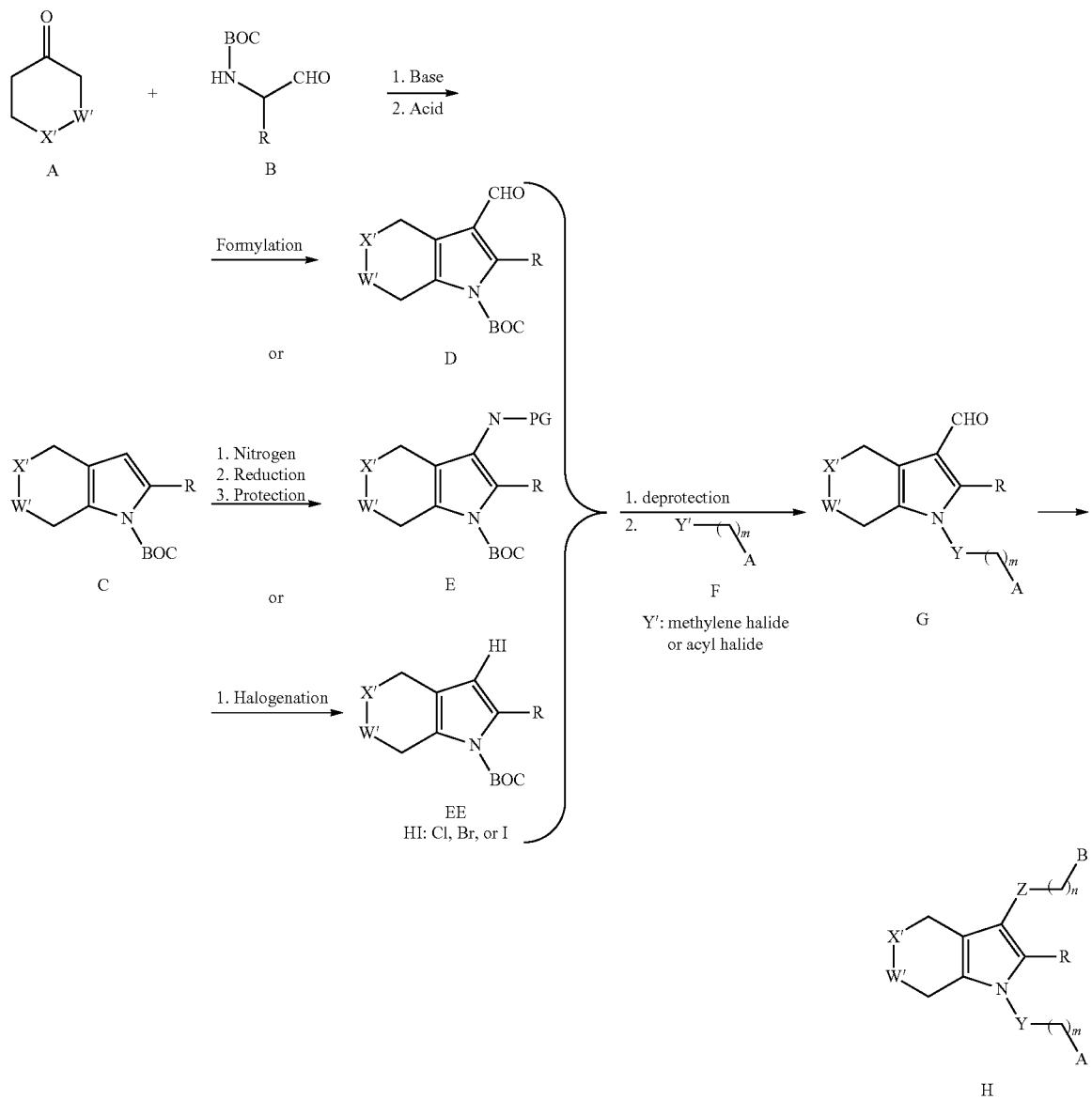

The compounds disclosed herein may be prepared by a number of methods known in the art. Scheme 1 depicts one example of a general method that may be employed. In this method, the starting ketone A is prepared using conventional alkylation of N-protected aminoacetaldehyde or a comparable method. The handle for Z is added by formylating the ring to obtain D, by nitration followed by reduction and protection to obtain E, or by halogenation to obtain EE. The ring protecting group on the ring nitrogen is then removed and —Y—(CH$_2$)$_m$-A is added via compound F to form G. If Y is heteroaryl, the ring nitrogen could be coupled to the appropriate halo-heteroaryl via a metal mediated coupling reaction.

The Z—(CH$_2$)$_n$—B moiety is then completed to form H depending upon the identity of Z. If Z CH$_2$, then the molecule may be completed via a Wittig or another carbon-carbon coupling followed by reduction or hydrogenation if necessary. If Z is C=O, then the aldehyde handle may be oxidized to a carboxylic acid, converted to an acyl halide and coupled to Z'—(CH$_2$)$_n$—B, where Z' is the appropriate metal or combination of metals. If Z is —C(O)NH—, the acyl chloride is reacted with an amine (Z' is NH$_2$) with a base or catalyst if appropriate. If Z is a protected amine, the amine is deprotected and reacted with the appropriate acyl chloride (Z' is halo-C(O)—). If Z is heteroaryl, EE is coupled to the appropriate heteroaryl agent via Suzuki, Stille, or a similar method, to obtain the final product. Alternatively, a condensation reaction utilizing the aldehyde handle, or an ester, amide, or hydrazide derivative might be employed.

An example of one method falling within general Scheme 1 is depicted in scheme 2 below.

Scheme 2

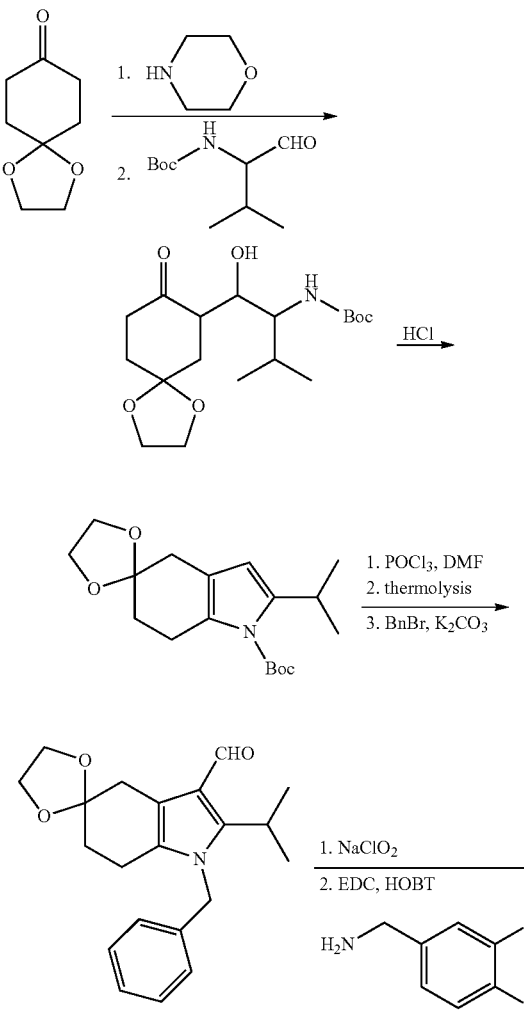

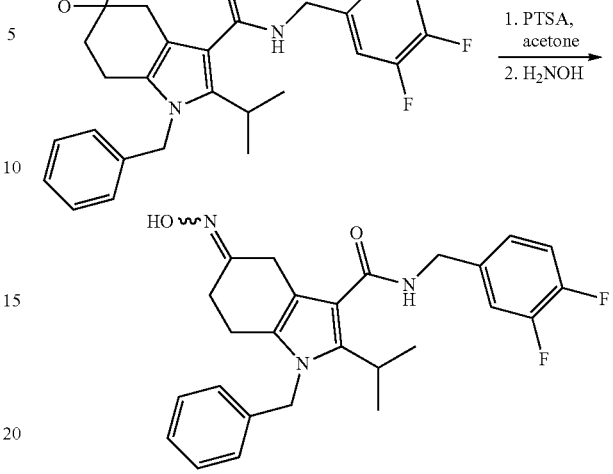

These compounds may be assessed for their ability to activate or block activation of the human S1P3 receptor in T24 cells stably expressing the human S1P3 receptor by the following procedure. Ten thousand cells/well are plated into 384-well poly-D-lysine coated plates one day prior to use. The growth media for the S1P3 receptor expressing cell line is McCoy's 5A medium supplemented with 10% charcoal-treated fetal bovine serum (FBS), 1% antibiotic-antimycotic and 400 μg/ml geneticin. On the day of the experiment, the cells are washed twice with Hank's Balanced Salt Solution supplemented with 20 mM HEPES (HBSS/Hepes buffer). The cells are then dye loaded with 2 uM Fluo-4 diluted in the HBSS/Hepes buffer with 1.25 mM Probenecid and incubated at 37° C. for 40 minutes. Extracellular dye is removed by washing the cell plates four times prior to placing the plates in the FLIPR (Fluorometric Imaging Plate Reader, Molecular Devices). Ligands are diluted in HBSS/Hepes buffer and prepared in 384-well microplates. The positive control, Sphingosine-1-Phosphate (SIP), is diluted in HBSS/Hepes buffer with 4 mg/ml fatty acid free bovine serum albumin. The FLIPR transfers 12.5 μl from the ligand microplate to the cell plate and takes fluorescent measurements for 75 seconds, taking readings every second, and then for 2.5 minutes, taking readings every 10 seconds. Drugs are tested over the concentration range of 0.61 nM to 10,000 nM. Data for Ca$^{+2}$ responses are obtained in arbitrary fluorescence units and not translated into Ca$^{+2}$ concentrations. IC$_{50}$ values are determined through a linear regression analysis using the Levenburg Marquardt algorithm.

What is claimed is:
1. A compound having a formula:

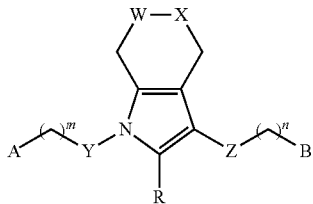

wherein m and n are independently 0, 1, or 2;
W and X are independently O, C=O, C(R$^2$)$_2$, S, S(O), SO$_2$, N—R$^2$, or C=NR$^2$, wherein R$^2$ is independently H, OH, C$_{1-6}$ alkyl, —O—(C$_{1-6}$ alkyl), or —NH—(C$_{1-6}$ alkyl);

Y is CH$_2$, C=O, —NHC(O)—, or heteroaryl having a formula C$_{1-6}$H$_{0-11}$N$_{0-3}$O$_{0-2}$S$_{0-2}$F$_{0-1}$Cl$_{0-1}$Br$_{0-1}$;

Z is CH$_2$, CHOH, C=O, —C(O)NH—, —NHC(O)—, or heteroaryl having a formula C$_{1-6}$H$_{0-11}$N$_{0-3}$O$_{0-2}$S$_{0-2}$F$_{0-1}$Cl$_{0-1}$Br$_{0-1}$;

A and B are independently aryl or heteroaryl having a formula C$_{1-12}$H$_{0-29}$N$_{0-4}$O$_{0-6}$S$_{0-4}$F$_{0-6}$Cl$_{0-4}$Br$_{0-4}$I$_{0-4}$; and R is C$_{1-6}$ hydrocarbyl.

2. The compound of claim 1 wherein W is CH$_2$.

3. The compound of claim 2 wherein X is CH$_2$OH, C=O, or C=N(OH).

4. The compound of claim 1 wherein A is phenyl, thienyl, or pyridinyl.

5. The compound of claim 1 wherein A is phenyl.

6. The compound of claim 1 wherein B is phenyl or pyridinyl.

7. The compound of claim 6 wherein B is phenyl.

8. The compound of claim 5 wherein B is phenyl.

9. The compound of claim 1 wherein R is methyl, ethyl, n-propyl, or isopropyl.

10. The compound of claim 8 having a formula:

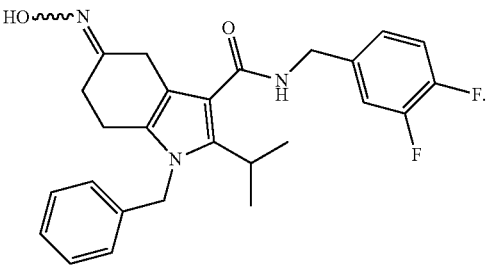 [SMILES: CC(C)c1c(C(=O)NCc2ccc(F)c(F)c2)c2c(n1Cc1ccccc1)CCC(=NO)C2]

* * * * *